US006180410B1

(12) United States Patent
Gerstel et al.

(10) Patent No.: US 6,180,410 B1
(45) Date of Patent: Jan. 30, 2001

(54) METHOD AND SYSTEM FOR PREPARING SAMPLES FOR GAS CHROMATOGRAPHY

(75) Inventors: Eberhard Gerstel; Ralf Bremer, both of Mulheim (DE)

(73) Assignee: Gerstel GmbH (DE)

( * ) Notice: Under 35 U.S.C. 154(b), the term of this patent shall be extended for 0 days.

(21) Appl. No.: 09/049,243

(22) Filed: Mar. 27, 1998

(30) Foreign Application Priority Data

Mar. 28, 1997 (DE) .............................................. 197 13 205

(51) Int. Cl.[7] ........................... G01N 30/02; G01N 30/14
(52) U.S. Cl. ................................ 436/54; 73/23.41; 95/89; 96/105; 422/70; 422/89; 422/100; 436/161; 436/180
(58) Field of Search ................................ 422/70, 89, 100; 436/161, 54, 180; 95/89; 96/105; 73/23.41, 23.42, 61.55, 61.56

(56) References Cited

PUBLICATIONS

David et al., LaborPraxis, vol. 21, No. 5, pp. 82–86, 1997.*
Ramsteiner, J. Chromatogr., vol. 393, No. 1, pp. 123–131, 1987.*
Chemical Abstracts, Abstract No. 1997:341634. David et al., LaborPraxis, vol. 21, No. 5, pp. 82–86, 1997.*
Chemical Abstracts, Abstract No. 1987:402049. Ramsteiner, J. Chromatogr., vol. 393, No. 1, pp. 123–131, 1987.*

* cited by examiner

*Primary Examiner*—Jan Ludlow
(74) *Attorney, Agent, or Firm*—Patterson, Thuente, Skaar & Christensen, P.A.

(57) ABSTRACT

The invention relates to a method and device for preparing samples for gas chromatography, the sample material being guided through a liquid chromatograph (1) by means of a solvent and being monitoring by means of a detector (2), and, on the basis of the detector (2) recognizing a chromatographic region of interest, the sample material of this region being removed from the stream of sample material leaving the liquid chromatograph (1) and being analyzed by gas chromatography. In this case, the stream of sample material leaving the liquid chromatograph (1) is guided through a flow-through cuvette (4), and the removal is carried out, until the end of the chromatographic region of interest, via a syringe (18) which, when the sample material of the region of interest reaches the flow-through cuvette (4), is introduced into the stream of sample material guided through the flow-through cuvette (4) and is drawn upwards at a predetermined ratio to the transport rate of the stream of sample material.

6 Claims, 2 Drawing Sheets

METHOD AND SYSTEM FOR PREPARING SAMPLES FOR GAS CHROMATOGRAPHY

BACKGROUND OF THE INVENTION

The invention relates to a method and a system preparing samples for gas chromatography.

In order to prepare samples for gas chromatography, it is known to connect a liquid chromatograph (LC) upstream of the gas chromatograph (GC). For this purpose, in on-line operation, a valve circuit with fixed bypass injector is used. Immediately after passing an LC detector, the sample material is removed from the LC and conveyed via a transfer line to a complicated valve device which is connected in such a way that the sample material contained in the bypass injector is flushed directly into a gas-chromatography capillary column using a carrier gas. However, such columns have only a limited sample capacity, so that this operation is possible only by employing complicated coupled-column technique comprising up to three series-connected capillary columns, firstly a gas-chromatographically inactive column for holding the sample material, then a precolumn for blending out the solvent, and finally a main column for the chromatographic separation. A so-called early-vapor exit is situated between the latter two columns. In this case, the bypass injector can only be changed by means of costly modification of the device. There are not possibilities for variation, and only the start of feed to the inactive column, and hence the selection of the starting point of a chromatographic region of interest, can be influenced.

In off-line operation, the sample material, downstream of the LC, is in sample bottles of a fraction collector, in order then to be analyzed further in a conventional manner.

SUMMARY OF THE INVENTION

The object of the invention is to provide a method and a system for preparing samples for gas chromatography, the sample material being guided through a liquid chromatograph by means of a solvent and being monitored by means of a detector, and, on the basis of the detector recognizing a chromatographic region of interest, the sample material of this region being removed from the stream leaving the liquid chromatograph and being analyzed by gas chromatography, characterized in that the stream of sample material leaving the liquid chromatograph is guided through a flow-through cuvette, and the removal is carried out, until the end of the chromatographic region of interest, via a syringe, which is introduced into a flow-through cuvette and is drawn upwards at a predetermined ratio to the transport rate of the stream when that region of the sample material which is of interest has reached the flow-through cuvette.

A feature of the invention is that it allows simple and variable preparation of samples.

As a result, the quantity of sample material which can be used for gas chromatographic analysis is variable and not constant. The removal of the sample material which is to be analyzed by gas chromatography is both very simple and the apparatus is simple.

Further configurations of the invention can be found in the following description and the subclaims.

The invention is explained in more detail below with reference to exemplary embodiments which are illustrated in the appended drawings, in which:

DETAILED SPECIFICATION

The device illustrated comprises a liquid chromatograph 1 with a detector 2, liquid sample material, substances dissolved in a solvent, being conveyed through the liquid chromatograph by means of a pump, passing by the detector 2 and after passing the detector 2 being output into a preferably flexible, transfer line 3, which in order to avoid falsification of the results may be deactivatable, so as to be inactive with respect to substances in the sample material flowing through. The transfer line 3 is connected to a collection vessel (not shown) via a flow-through cuvette 4.

Figure 1:
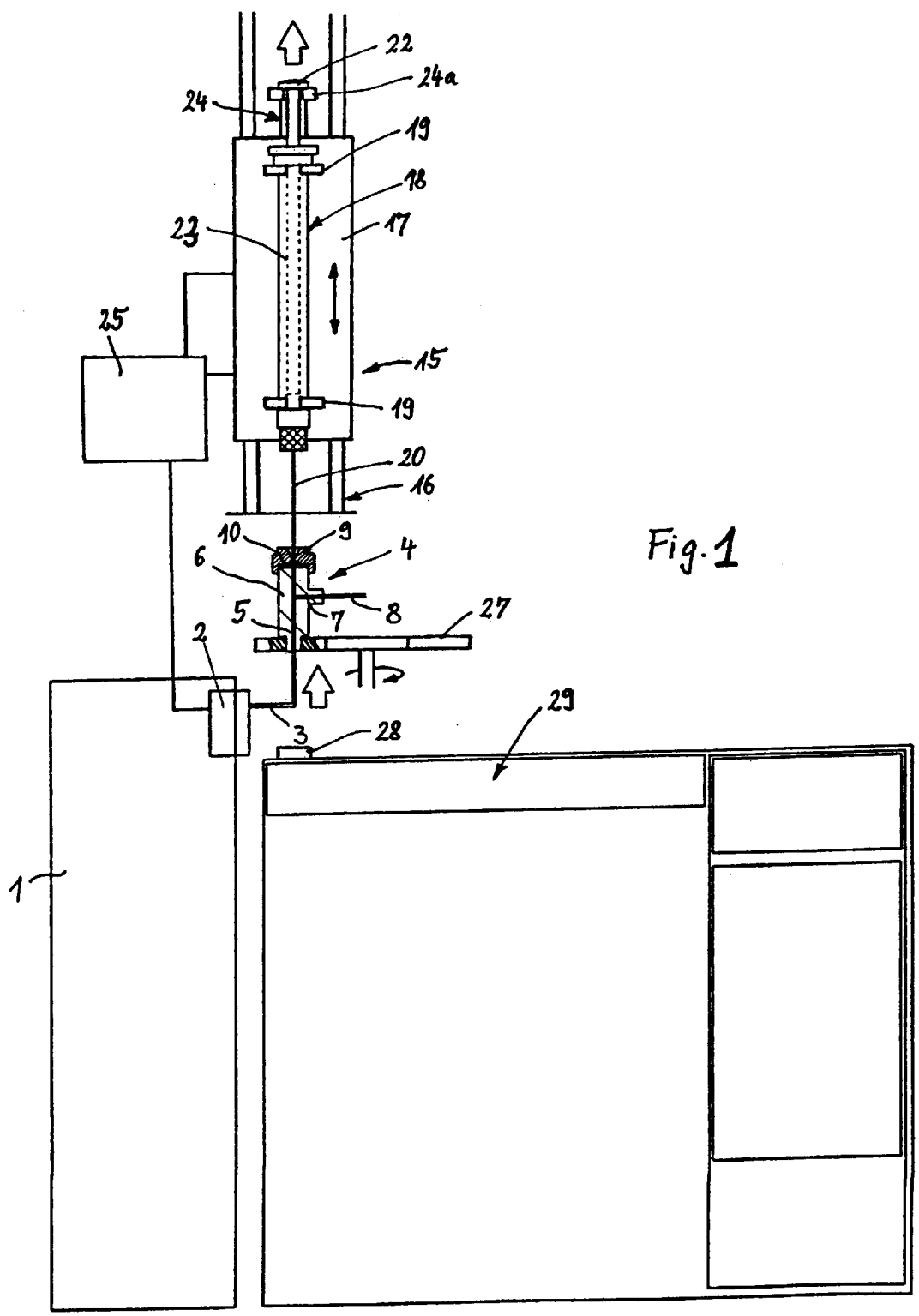
FIG. 1 is a diagrammatic view of a device for preparing samples for gas chromatography.

In the exemplary embodiment illustrated in FIG. 1, the flow-through cuvette 4 is formed by a cuvette body 6 which is provided with a through-bore 5, a transverse bore 7 opening out into the through bore 5. The transfer line 3 opens out into the lower end of the through-bore 5, while the transverse bore 7 is connected to a discharge line 8 which leads to the collection vessel. The line 3, 8 and the bore 5, 7 expediently have narrow, constant internal diameters, in such a manner that there is virtually no cross-mixing of the sample material conveyed therein.

Figures 2A, 2B:
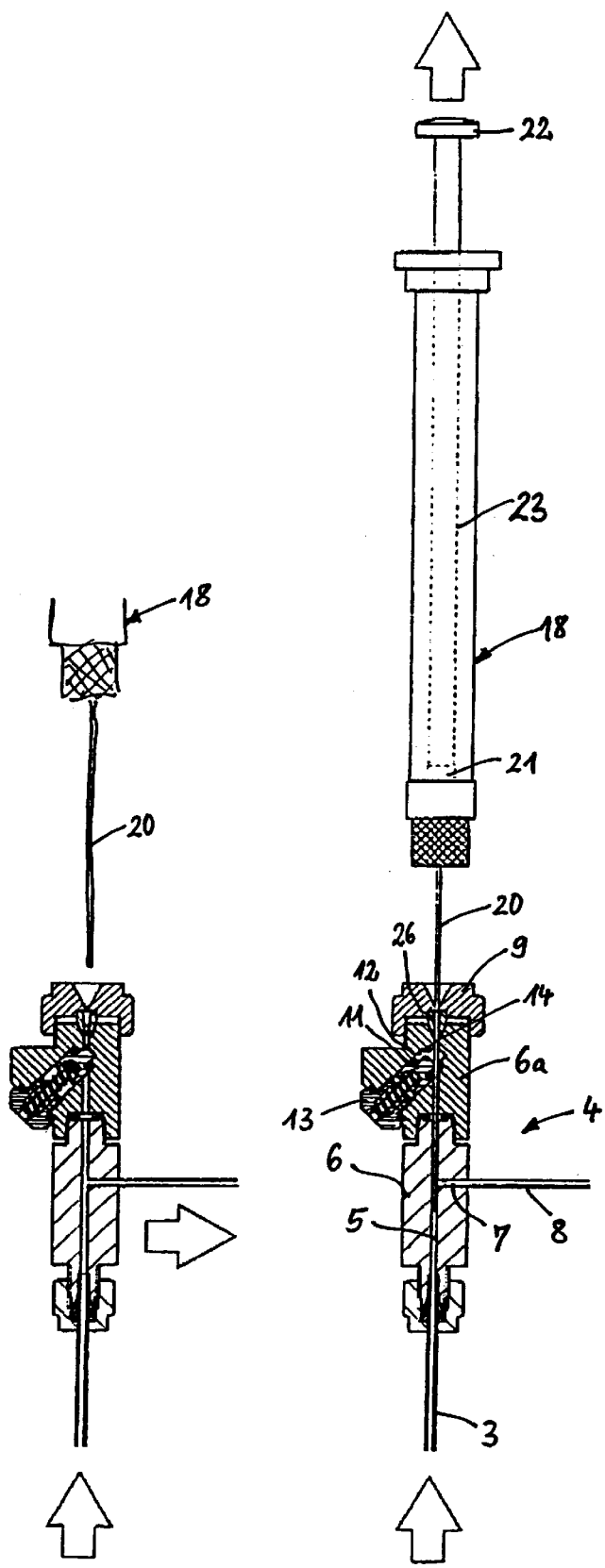
FIGS. 2a and 2b are cross-sectional view of a further embodiment.

At the top, the cuvette body 6 in accordance with FIG. 1 has a septum 10 which is clamped in by means of a screwed-on mouthpiece 9. As an alternative, as illustrated in FIGS. 2a, 2b, the cuvette body 6, or an attachment 6a thereon, may also include a valve body 11 which closes off the bore 5 at the top, and in a guide 12, in a spring-loaded manner with respect to a stopper 13, has an end face which runs at an angle to the bore 5 and with respect to which the sealing surface is set back. In this case, in the closed position the sealing surface interacts with an annular stop surface 14, which surrounds the bore 5, in the attachment 6a.

Before commencing operation, the flow-through cuvette 4 is flushed with inert solvent in the unsealed state, in order to eliminate any air pockets. In operation, sample material then flows out of the liquid chromatograph 1, through the transfer line 3, the flow-through cuvette 4 and the discharge line 8, into the collection vessel, while the inert solvent stands in the region of the bore 5 between the transverse bore 7 and the septum 10 or the valve body 11.

The device furthermore comprises an insertion device 15, which comprises, for example, a frame 16 with a vertically displaceable holding carriage 17 for a syringe 18. The holding carriage 17 has a mount 19 for vertically holding the syringe 18 with the needle 20 pointing downwards and can be moved up and down by a predetermined distance by means of a drive (not shown) in such a manner that the needle 20 of the syringe 18 can be introduced into the bore 5 either through the septum 10, or, by pressing back the valve body 11, past the valve body, and approximately beyond the opening of the transverse bore 7.

The syringe 18 contains a piston 21, which is connected to a piston rod 23 which can be guided outwards and on the end side has a head 22. A draw-up device 24, which may comprise, for example, a gripper 24a, acts on the piston rod 23, which gripper can be used to pull the piston rod 23 upwards with respect to the stationary syringe 18, so as to draw the syringe 18 upwards, by means of a drive which is part of the insertion device.

The detector 2 is coupled to a computerized control system 25, which can be used to input the start and end of a chromatographic region of the sample material, the beginning of which is to be established by the detector 2 and the length of which depends on the region of interest of a particular chromatogram.

When the detector 2 detects the beginning of the chromatographic region of interest of the sample material, it uses the control system 25 to move the syringe 18 into the flow-through cuvette 4. Since the rate at which the sample material is conveyed through the liquid chromatograph 1 and the flow-through cuvette 4 is known, owing to the pump capacity and the cross-section of flow, it is also known when the region of interest will appear in the flow-through cuvette 4, so that the syringe 18 is introduced into the flow-through cuvette 4 in accordance with this time.

Then, the syringe 18 is drawn upwards, via the control system 25, at a constant rate which is predetermined by the control system 25. Normally, this takes place in accordance with the stream of sample material, so that all the sample material within the chromatographic range of interest is taken up by the syringe 18. However, if the region selected is too large, so that the syringe 18 cannot hold all the sample material conveyed in the associated time period, this can advantageously be calculated by the control system 25 and indicated to the user, so that either the region is limited in a suitable manner by freshly inputting its beginning and end, if possible, or else sample material is transferred in a split ratio into the syringe 18, while the remaining part flows past the needle 20 of the syringe 18 and into the discharge line 8. In this case, the draw-up rate is reduced by the factor of the splitting ratio. This ensures that sample material is drawn up through the syringe 18 in accordance with the representative chromatogram section of interest. In this case, the needle 20 is sealed in a gastight manner with respect to the outside by means of the septum 10 or another seal 26 between mouthpiece 9 and cuvette body 6.

Expediently, the flow-through cuvette 4 may be mounted on a turntable 27 which has a cutout via which the syringe 18, after the sample preparation has taken place, can feed its contents into a feed device 28 of a gas chromatograph 29 which has a capillary column. The feed device may, for example, be a cold feed device 28, for example in accordance with EP-0,451,566-A2 or in accordance with DE-196 53 406 C1. It is expedient for solvent to be blended out first, after which the sample material is transferred, by means of carrier gas, to the capillary column of the gas chromatograph 29 and is analyzed.

If appropriate, a plurality of flow-through cuvettes 4 may be arranged on the turntable 27.

It the solvent used for the liquid chromatography, for example water, is unsuitable for the gas chromatography, the contents of the syringe 18 may initially be placed in a sample bottle, where they are redissolved in a solvent which is suitable for the gas chromatography, for example hexane, so that two separate layers, situated one above the other, are formed, of which the layer which is for gas chromatography is removed again and is fed into the gas chromatograph 29 by means of a syringe which is introduced into the feed device 28.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the invention scope of the In the claims:

1. A method for preparing samples for gas chromatography comprising the steps of:
    a) guiding sample material through a liquid chromatograph with a detector by a solvent;
    b) discharging the sample material from the liquid chromatograph in a stream at a transport rate through a flow-through cuvette;
    c) recognizing by way of the detector a chromatographic region of interest in the stream; and
    d) withdrawing the chromatographic region of interest in the stream of the sample material into a syringe at a predetermined ratio to the transport rate of the stream when that region has reached the flow-through cuvette.

2. The method according to claim 1 further comprising the step of placing the sample material removed by the syringe in a sample bottle where it is redissolved in a solvent which is suitable for the gas chromatography.

3. The method of claim 1 further comprising the step of feeding the sample material removed from the syringe by a carrier gas via a cold feed device to a gas chromatography column.

4. The method according to claim 3 further comprising the step of placing the sample material removed by the syringe in a sample bottle where it is redissolved in a solvent which is suitable for the gas chromatography.

5. The method of claim 3 further comprising the step of discharging the solvent in the syringe before the sample material is fed into the gas chromatography column.

6. The method according to claim 5 further comprising the step of placing the sample material removed by the syringe in a sample bottle where it is redissolved in a solvent which is suitable for the gas chromatography.

* * * * *